United States Patent [19]

Shippert

[11] Patent Number: 4,895,559
[45] Date of Patent: Jan. 23, 1990

[54] NASAL PACK SYRINGE

[76] Inventor: Ronald D. Shippert, 4975 S. Albion St., Littleton, Colo. 80121

[21] Appl. No.: 255,461

[22] Filed: Oct. 11, 1988

Related U.S. Application Data

[63] Continuation of Ser. No. 81,658, Aug. 4, 1987, abandoned.

[51] Int. Cl.[4] .............................................. A61F 13/20
[52] U.S. Cl. ....................................... 604/15; 604/904
[58] Field of Search ..................... 604/11, 13, 15–16, 604/18, 94, 904, 264, 285, 286; 128/325

[56] References Cited

U.S. PATENT DOCUMENTS

| | | | |
|---|---|---|---|
| 604,393 | 5/1898 | Hooker | 604/218 |
| 636,637 | 11/1899 | Cooke | 604/13 |
| 682,090 | 9/1901 | Lee | 604/13 |
| 702,570 | 6/1902 | Lohlein | 604/15 |
| 702,997 | 6/1902 | Pugh | 128/263 |
| 1,235,095 | 7/1917 | Beck | 128/325 |
| 1,562,656 | 11/1925 | Park | 604/13 |
| 2,524,195 | 10/1950 | Hoover | 128/325 |
| 2,691,985 | 10/1954 | Newsom | 128/325 |
| 2,761,449 | 9/1956 | Bletzinger | 604/904 |
| 3,015,332 | 1/1962 | Brecht | 604/15 |
| 3,049,125 | 8/1962 | Kriwkowitsch | 128/325 |
| 3,101,713 | 8/1963 | Sargent | 604/16 |
| 3,103,929 | 9/1963 | Brecht | 604/17 |
| 3,433,225 | 3/1969 | Voss et al. | 604/14 |
| 3,507,274 | 9/1970 | Soichet | 604/218 |
| 3,570,494 | 3/1971 | Gottschalk | 128/325 |
| 3,628,534 | 12/1971 | Donohue | 604/904 |
| 3,674,026 | 7/1972 | Werner et al. | 604/14 |
| 3,712,305 | 1/1973 | Wennerblon et al. | 604/904 |
| 3,717,149 | 2/1973 | Morane | 604/12 |
| 3,765,416 | 10/1973 | Werner et al. | 604/14 |
| 3,850,176 | 11/1974 | Gottschalk | 128/325 |
| 3,971,378 | 7/1976 | Krantz | 604/370 |
| 4,030,504 | 6/1977 | Doyle | 128/325 |
| 4,291,696 | 9/1981 | Ring | 604/16 |
| 4,411,647 | 10/1983 | Sakurai et al. | 604/16 |
| 4,479,791 | 10/1984 | Sprague | 604/14 |
| 4,536,178 | 8/1985 | Lichstein | 604/15 |
| 4,676,773 | 6/1987 | Sheldon | 604/16 |
| 4,755,166 | 7/1988 | Olmstead | 604/904 |

Primary Examiner—C. Fred Rosenbaum
Assistant Examiner—Sharon Rose
Attorney, Agent, or Firm—Sheridan, Ross & McIntosh

[57] ABSTRACT

A nasal pack syringe is provided that includes a barrel, a plunger, an expandable, absorbent packing material, and a suture for retrieval of the packing material. The barrel is substantially rectangular in cross-section. The dimensions of the barrel and packing material are influenced by the dimensions of the human nasal cavity. The barrel and packing material are of sufficient length to allow penetration as far as the posterior wall of the nasopharynx. The barrel has ribs projecting from an interior wall thereof to facilitate movement of the packing material and a notch for holding the suture to avoid any obstruction during the movement of the packing material relative to the barrel. The plunger has a split end to assure a tight fit between the plunger and the barrel. In using the nasal pack syringe, the plunger is moved to push the packing material from the barrel into the patient's nasal cavity. The packing material expands upon contact with blood. The packing material absorbs the blood to prevent aspiration of the blood by the patient. Once expanded, the packing material applies hemostatic pressure to ruptured vessels to arrest the flow of blood. Retrieval of the packing material is accomplished by the suture attached to the packing material.

4 Claims, 2 Drawing Sheets

NASAL PACK SYRINGE

This is a continuation of application Ser. No. 07/081,658, filed Aug. 4, 1987, now abandoned.

FIELD OF THE INVENTION

This invention relates to the treatment of nasal hemorrhages and more particularly to a product which facilitates the insertion of packing material into a nasal cavity.

BACKGROUND OF THE INVENTION

Nasal hemorrhaging is commonly treated by packing the nasal cavity with an absorbent material. The absorbent material serves two purposes. First, it absorbs the blood thereby preventing possible aspiration of the blood by the patient. Second, it averts the flow of blood by applying pressure to the ruptured blood vessel thereby acting as a hemostat.

At present, there are a number of devices which apply hemostatic pressure to control a nasal hemorrhage and absorb blood associated with the hemorrhage. However, several of these devices require that they be manually inserted. For example, U.S. Pat. No. 4,030,504 to Doyle issued June 21, 1977 and entitled "Nasal Hemostat And Method Of Construction of Nasal Hemostat" employs an expandable absorbent material contoured to conform to the nasal cavity, but which must be inserted and positioned by hand.

Also, typical prior art devices must be formed or adapted at the time of use. For example, a surgeon will typically trim a piece of expandable absorbent material to the appropriate size, attach a suture to the absorbent material in order to facilitate retrieval, and manually insert the device into the patient's nasal cavity. The absorbent material expands upon contact with the blood. This expansion results in hemostatic pressure being applied to the ruptured blood vessel thereby arresting the flow of blood. The absorbent material is then retrieved from the nasal cavity by means of the attached suture.

The prior art devices require a significant amount of manual manipulation, are time consuming to use, and result in a significant amount of patient discomfort. Accordingly, the need exists for a device which can quickly, relatively painlessly, and with a minimum of manual manipulation inject an expandable absorbent material into a hemorrhaging nasal cavity.

An example of other body fluid-absorbing devices, which are used in a different application, are the catamenial devices. Such devices are described in U.S. Pat. No. 3,015,332 to Brecht issued Jan. 2, 1962 and Entitled "Applicator", U.S. Pat. No. 3,103,929 to Brecht issued Sept. 17, 1963 and entitled "Catamenial Device"; U.S. Pat. No. 3,101,713 to Sargent issued Aug. 27, 1963 and entitled "Tampon Applicator"; and U.S. Pat. No. 3,433,225 to Voss issued Mar. 18, 1969 and entitled "Hygienic Devices and Methods of Making The Same". These devices inject an absorbent material into the female vaginal cavity during menstruation. A barrel which is circular in cross section, and a cylindrical plunger constitute the means for injecting the absorbent material. However, these devices would be inappropriate for use in the nasal cavity for several reasons. First, the absorbent material used in these catamenical devices is meant strictly to absorb menstrual blood flow. The absorbent material in these catamenical devices is not meant to apply hemostatic pressure. Second, since the bone and cartilage structures of the nasal cavity define a substantially rectangular cross section, the circular cross section of the barrel and absorbent material used in the catamenical devices would be inappropriate for use in the nasal cavity. Third, the length of absorbent material used in the catamenial devices would be inadequate for use in the nasal cavity.

SUMMARY OF THE INVENTION

A primary objective of the present invention is to provide a speedY, painless, and inexpensive means of delivering packing material to a patient's nasal cavity in order to provide clotting of ruptured blood vessels by hemostatic pressure. This is accomplished by injecting an expandable absorbent, packing material into the patient's nasal cavity by means of a syringe-like device.

The nasal pack syringe of the present invention includes a barrel, a plunger, an expandable packing material which fits into the barrel for absorbing blood and a suture attached to the packing material to facilitate retrieval.

The barrel is made of an inexpensive plastic material and is essentially rectangular in cross section. The rectangular cross section is influenced by the fact that the vertical dimension of the nasal cavity exceeds its lateral dimension. Likewise, the barrel is sufficiently long enough to allow penetration as far as the posterior wall of the nasopharynx. A flange is incorporated about one end of the barrel to provide a means for gripping the syringe. In addition, the flange incorporates a small notch that receives a portion of the suture during the injection procedure. The notch acts to hold the suture and thereby prevents the suture from binding in the barrel as the packing material is pushed from the barrel using the plunger. Additionally, a set Of ribs is longitudinally disposed about the interior of the barrel to minimize the friction produced at the interface defined by the barrel and the packing material. Reduction of this frictional component facilitates the quick and easy insertion of the packing material into the nasal cavity.

The plunger, like the barrel, is fabricated from inexpensive plastic material and is rectangular in cross section. An enlarged member is formed at one end of the plunger to provide a comfortable platform for applying pressure to the plunger. The other end of the plunger, the end which is received into a barrel shaft, is split such that a pair of prongs are created. These prongs extend laterally outward from the barrel shaft such that they are slightly wider than the shaft. The purpose of the prongs and slit formed therebetween is to generate sufficient friction to prevent the plunger from easily falling out of the barrel, but not so much friction that the sliding action of the plunger in the barrel is unduly inhibited.

The packing material is rectangular in cross section in order to conform to the shape of the barrel and is sufficiently long enough to extend from the nasal opening to the posterior wall of the nasopharynx. Prior to use, the packing material is in a compressed state. This characteristic alone enhances the ease with which packing material can be introduced into the nasal cavity. However, proper positioning of the packing material takes considerable time and prolongs patient discomfort. Consequently, injecting the packing material by means of the nasal pack syringe eliminates these concerns. The packing material once inserted in the patient's nasal cavity expands upon contact with the blood or other nasal fluid. This expansion serves two-fold purpose of absorbing the liquid and applying hemostatic pressure to ruptured blood vessels.

A suture is attached to the packing material to facilitate retrieval. The suture is attached to the end of the packing material nearest the nasal cavity opening. Once the packing material is properly positioned in the patient's nasal cavity, the suture is taped to the patient's face. After the packing material has served its purpose of absorbing blood and providing hemostatic pressure it can be removed by gently pulling the suture forward.

Use of the nasal pack syringe is easily accomplished and enhances patient comfort. The barrel containing the compressed absorbent packing material is inserted an appropriate distance into the patient's nasal cavity. The plunger is then used to force the packing material out of the barrel. As the plunger is being activated the barrel is being withdrawn. Consequently, the packing material is expelled from the barrel into the patient's nasal cavity. The suture attached to the absorbent material is then secured to the patient's face. Once the absorbent material has served its purposes of absorbing blood and contributing to clotting it can be removed by means of the attached suture.

In view of the foregoing summary description, a number of advantages of the present invention are easily recognized. A nasal pack syringe is disclosed for use in controlling bleeding in a nasal cavity. The barrel and packing material of the syringe are sized to function in an accommodating manner with the nasal cavity. The packing material performs two important functions, namely, absorbing liquid present in the nasal cavity and generating hemostatic pressure. The barrel has ribs for easy insertion of the packing material into the nasal cavity. A notch is also provided on a barrel flange to prevent or reduce unwanted obstruction by the suture inside the barrel during insertion of the packing material into the nasal cavity. The plunger has a split end to ensure suitable mating and movement with respect to a barrel shaft. The nasal pack syringe can be made in various sizes to accommodate for use after nose surgery, as well as being used in the case of a common nose bleed.

Additional advantages of the present invention will become readily apparent from the following description, when taken in conjunction with the accompanying drawings.

DETAILED DESCRIPTION OF THE PREFERRED EMBODIMENT

Figure 1:
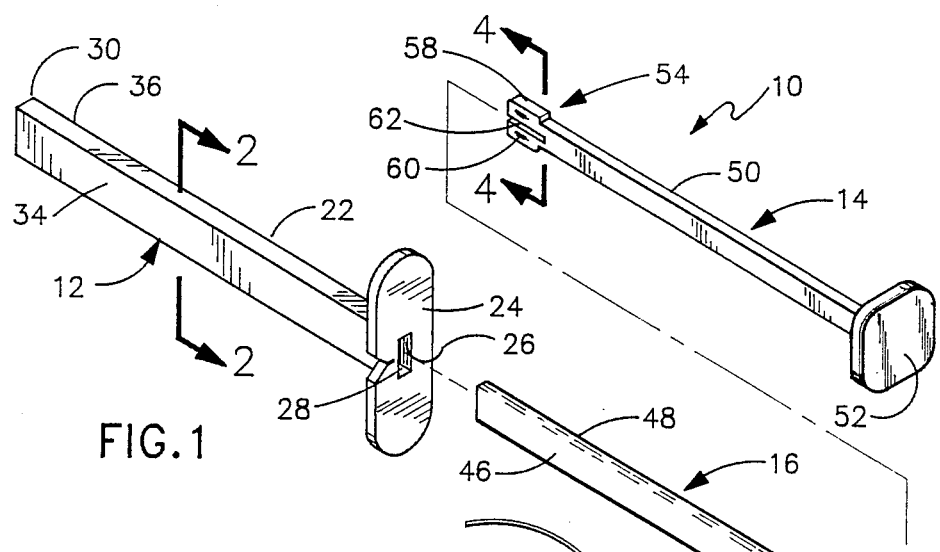
FIG. 1 is an exploded view showing the parts of the nasal pack syringe.

In accordance with the present invention, a nasal pack syringe 10 is provided to stop bleeding in a nasal cavity. With reference to FIG. 1, the nasal pack syringe 10 includes a barrel 12, a plunger 14, packing material 16, and a piece of suture 20.

Figure 2:
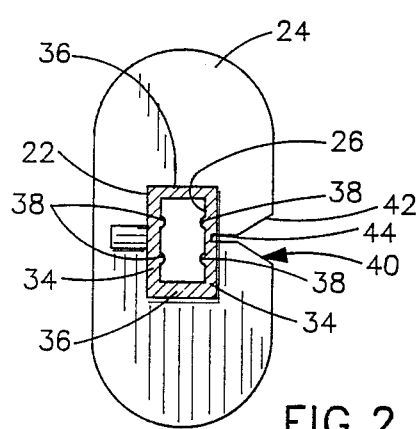
FIG. 2 is an enlarged, lateral, cross-sectional view of the barrel taken alone lines 2—2, of FIG. 1, illustrating the rectangular cross-section of the barrel shaft.
Figure 3:
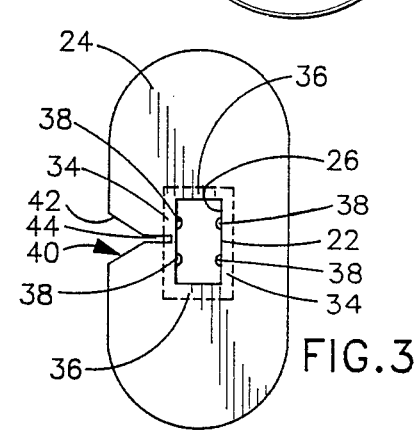
FIG. 3 is an enlarged, end view of the barrel illustrating the barrel flange, as well as the ribs formed in the barrel shaft and the notch formed in the barrel flange.

The barrel 12 includes a shaft 22 and a flange 24 formed integral with the shaft 22 at one end thereof. With reference also to FIGS. 2 and 3, the barrel 12 has a receiving space or bore 26 formed through portions of the shaft 22 and the flange 24. The bore 26 is provided to receive the packing material 16. In that regard, the barrel 12 has an inlet end 28, which is located at the flange 24, and an outlet end 30 which is located at the free end of the shaft 22.

The shaft 22 comprises two parallel wide sides 34, which are integrally interconnected by means of two parallel narrow sides 36. As best seen in FIGS. 2 and 3, ribs 38 are formed on the interior of the wide sides 34. In the preferred embodiment, there are two ribs 38 provided on each of the two wide sides 34. Each of the ribs 38 extends in a longitudinal direction along the shaft 22 and each extends for a substantial length of the shaft 22. The ribs 38 project into the bore 26 and are used in facilitating movement of the packing material 16 relative to the shaft 22, as will be subsequently explained in more detail. The shaft 22 with the wide and narrow sides 34, 36 has a substantially rectangular cross-section and, concomitantly, the bore 26 also has a substantially rectangular cross-section. This dimensional configuration is influenced by the size and shape of the typical human nasal cavity. That is, the nasal cavity, which is to receive the packing material 16, is greater in length in a vertical direction than it is in a lateral direction. Further, the shaft 22 is of a suitable length to allow the user or operator of the nasal pack syringe 10 to insert the packing material 16 at the desired depth in a nasal cavity, such as the posterior wall of the nasal nasopharynx.

With continued reference to FIGS. 2 and 3, the barrel flange 24 is enlarged in size over the shaft 22 for easy grasping of the barrel 12 by the operator when pushing or causing the packing material 16 to move using the plunger 14. The flange 24 also has a notch 40 formed at a peripheral edge thereof. The notch 40 is formed at about the mid-portion of the flange along its longitudinal extent. As best seen in FIGS. 2 and 3, the notch 40 has a tapering section 42 and a straight section 44. The tapering section 42 converges inwardly relative to the peripheral edge of the flange 24 and the straight section 44 is integral with the tapering section 42 and extends through the flange portion for a short distance into the shaft portion of the barrel 12. The notch 40 receives portions of the suture 20 and acts as a guide or retainer, at least for some of the time, during movement of the packing material 16 relative to the barrel 12. The depth of the notch 40, is intended to ensure that the suture 20 is held in the notch 40 until the packing material 16 is at a desired position or location relative to the barrel 12 during its outward movement relative to the barrel 12. In a preferred embodiment, the barrel 12, including the shaft 22, is made of a translucent plastic material whereby the user, if desired or suitable, can better observe movement of the packing material 16 relative to the barrel 12.

As best seen in FIG. 1, the packing material 16 is of a size and shape to be comfortably positioned in and move through the receiving space 26 formed in the barrel 12. In particular, similar to the shaft 22, the packing material 16 has two, spaced wide sides 46 and two spaced narrow sides 48 wherein the narrow sides 48 interconnect the wide sides 46. In the illustrated embodiment of FIG. 1, the length of the packing material 16 is intended to be sufficient to extend from the posterior wall of the nasopharynx to the nostril openings. A source of packing material 16 is identified by the trademark "Merocel." As will be explained in greater detail herein, the packing material 16 is made of an expandable, absorbent material for use in absorbing blood or other liquid that may be present in a nasal cavity.

The suture 20 is attached to the packing material 16 at the end thereof, which is to be contacted or engaged by the plunger 14. The suture 20 is of a length to permit ready attachment of the end of the suture 20 to the face of the patient receiving the packing material 16. The diameter or cross-section of the suture 20 is of a size to be received by the notch 40 of the barrel 12. This shape or size should be adequate to permit easy placement of the suture 20 into the straight section 44 while permitting length-wise directional movement of the suture 20 through the straight section 44 as the packing material 16 is being injected or inserted into a nasal cavity.

Figure 4:
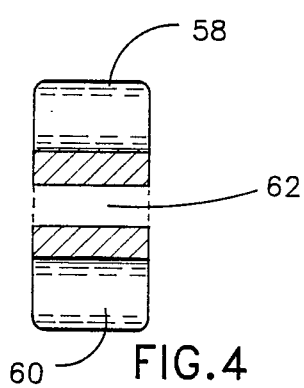
FIG. 4 is an enlarged, lateral, cross-sectional view of the plunger tip, taken along lines 4—4 of FIG. 1, showing the retention unit.

With reference also to FIG. 1, the plunger 14 of the nasal pack syringe 10 is comprised of a shaft 50, an enlarged member 52 and a retention unit 54. The enlarged member 52 is integrally formed at one end of the shaft 50 while the retention unit 54 is integrally formed at the opposite end of the shaft 50. The plunger shaft 50 is elongated and has a length comparable to the length of the barrel shaft 22. The enlarged member 52 is greater in size than the bore 26 of the barrel 12, while the plunger shaft 50 is dimensioned so that it can be received by and be movable relative to the bore 26 of the barrel 12. The enlarged member 52 is used by the operator of the nasal pack syringe 10 to push or force the packing material in a direction towards the outlet end 30 of the barrel 12. The retention unit 54 includes a pair of separated prongs or tip portions 58, 60. As best seen in FIG. 4, the two prongs 58, 60 are separated by a space or slit 62 formed in the end portion of the plunger 14. The lateral extent of each of the two prongs 58, 60 is greater than the lateral extent or width of the plunger 14.

The retention unit 54 serves to prevent the plunger 14 from unwanted disengagement from the barrel 12. The retention unit 54 also allows for easy, sliding movement of the plunger 14 relative to the barrel 12. The prongs 58, 60 are configured such that the distance or length between the exterior, longitudinal surfaces of the two prongs 58, 60 exceeds the corresponding dimension of the barrel bore 26. Because of this greater size, the prongs 58, 60 must be forced inwardly when the plunger shaft 50 is to be inserted into the barrel bore 26. The slit 62 is provided to permit this inward flexing of the prongs 58, 60, which flexion results due to the engagement or contact between the prongs 58, 60 and the narrow sides 36 of the barrel shaft 22. Once positioned in the barrel bore 26, the normal force produced by the tendency of the prongs 58, 60 to flex outward results in a resistance component being generated in the longitudinal direction relative to the barrel shaft 22. Consequently, the retention unit 54 causes sufficient friction in the longitudinal direction to prevent the plunger 14 from escaping or disengaging from the barrel 12, while at the same time not producing so much friction that the movement of the plunger 14 is inhibited.

Figure 5:
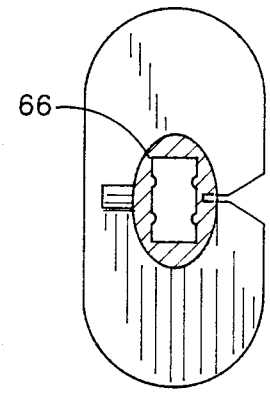
FIG. 5 is another embodiment of the present invention illustrating that the barrel shaft can be generally oval-shaped.

Another geometric configuration of the barrel 12 is illustrated in the embodiment of FIG. 5. Instead of a barrel shaft having a generally rectangular cross-section configuration, a barrel shaft 66 is illustrated as having a substantially oval-shaped configuration and cross-section. The oval barrel shaft 66 results in eliminating sharp corners at the outlet end of the barrel shaft 66. In such a configuration, the possibility that the barrel shaft 66 could cause irritation to the patient as it is being inserted in a nasal cavity is reduced.

Figure 6:
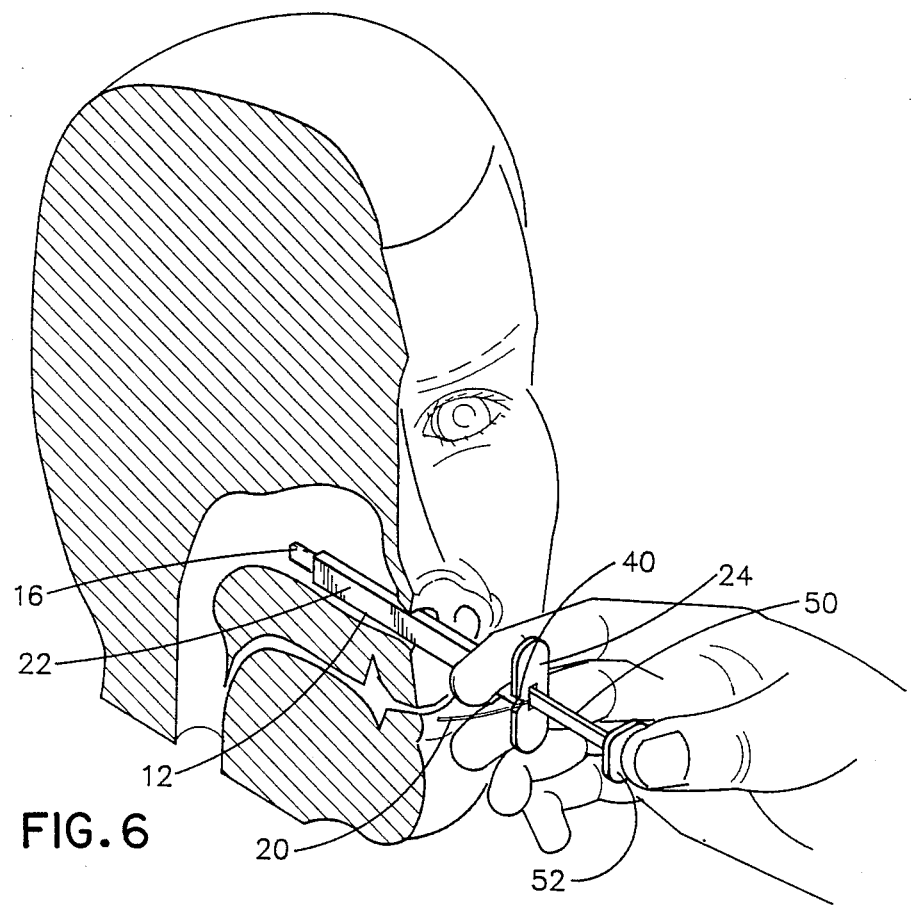
FIG. 6 illustrates the insertion of the packing material into a nasal cavity.
Figure 7:
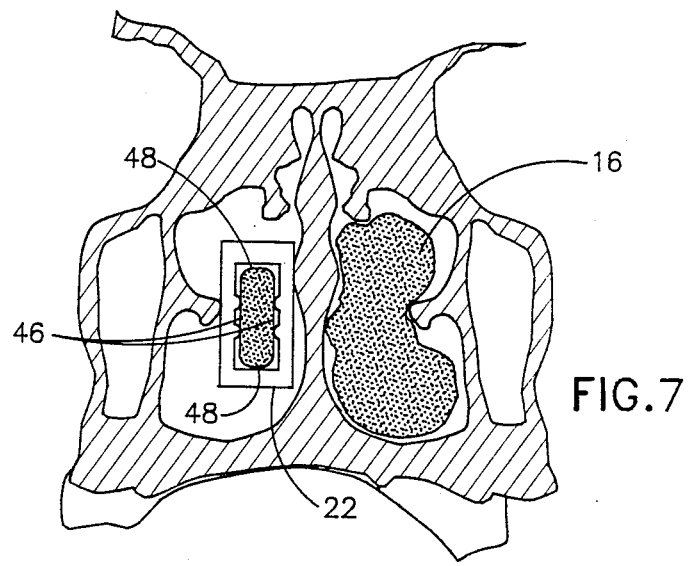
FIG. 7 is a cross-sectional view of a human nose illustrating in the left side nasal cavity the insertion of the compacted packing material and illustrating in the right side nasal cavity the expanded packing material after it has absorbed blood or other fluid.

In using the nasal pack syringe 10, particular reference is made to FIGS. 6 and 7. First, the assembled nasal pack syringe 10 with the packing material 16 contained in the barrel 12 together with portions of the plunger 14 including the retention unit 54 already positioned in portions of the barrel bore 26 as well as the suture 20 located in the notch 40, is removed from its sterile packaging. The user, such as a physician, grasps the nasal pack syringe 10 by engaging the barrel flange 24 With the middle and forefinger and by placing the thumb on the enlarged member 52 of the plunger 14. The outlet end 30 of the barrel 12, together with portions of the shaft 22 are positioned into the nasal cavity, which is to receive the packing material 16. As can be seen in FIG. 6, when inserting the portions of the nasal pack syringe 10 into the nasal cavity of interest, the wide sides 34 of the shaft 22 are substantially parallel to the vertical extent of the nasal cavity. As previously mentioned, this is the proper position because the vertical extent of the nasal cavity is greater than its lateral extent.

With the nasal pack syringe properly located relative to the nasal cavity, the user pushes or forces the packing material from the barrel shaft 22 and out of the outlet end 30 thereof for receipt by and positioning in the nasal cavity. During the time that the packing material 16 is being ejected from the barrel shaft 22, the ribs 38 are facilitating movement of the packing material 16 relative to the shaft 22 due to the reduced friction. That is, the ribs 38 serve to reduce the resistance created at the interface between the interior walls of the barrel shaft 22 and the packing material 16 by reducing the area of contact therebetween. In addition, the notch 40 guides the suture 20 and holds the suture 20 in place, at least during a portion of the movement of the packing material 16 along the barrel shaft 22. As a result, possible binding of the suture 20 in the barrel shaft 22 is prevented during movement of the packing material 16. Any binding could hamper the ejection of the packing material 16 from the barrel shaft 22 and, concomitantly, increase the time required to safely and accurately position the packing material 16 in the nasal cavity. Also during the insertion process using the nasal pack syringe 10, the retention unit 54 acts to properly maintain the plunger 14 along its desired path towards the outlet end SO of the barrel shaft 22.

As the packing material 16 is being ejected from the barrel outlet end 30, the user begins to withdraw barrel shaft portions from the nasal cavity, but continues to push on the enlarged member 52 of the plunger 14 until the packing material 16 is completely removed from the shaft 22. At this time and with the packing material 16 removed from the shaft 22, the suture 20 can be attached to the patient's face near or at the cheekbone using tape or some other suitable connecting element or article. The packing material 16 then performs the necessary two functions in the nasal cavity. Referring to FIG. 6, it absorbs the blood or other liquid in the nasal cavity and, as the packing material absorbs the liquid, it expands to occupy a significant amount of space in the nasal cavity. At this time, also, the expanded packing material 16 exerts hemostatic pressure to the ruptured blood vessels thereby preventing or reducing further bleeding. After the packing material 16 has served its purposes, it can be removed using the suture 20 by carefully pulling on the suture 20 until the packing material 16 is removed from the nasal cavity.

While the apparatus and method herein described constitutes the preferred embodiment of the invention, it is to be understood that the invention is not limited to this exact apparatus and method and that changes can be made without departing from the scope of the invention, which is defined in the appended claims.

What is claimed is:

1. A nasal pack syringe, comprising:
   packing material having an end surface for insertion into a nasal cavity and being of a first size to facilitate insertion into said nasal cavity, said packing material being capable of absorbing fluid and expanding to a second size upon contact with said fluid in order to apply pressure to ruptured blood vessels in order to reduce the flow of blood in the nasal cavity, said packing material being single piece and rigid and having a cross-section wherein said cross-section substantially throughout the length of said packing material has a larger dimension in a first direction than the largest dimension of said cross-section in a direction substantially perpendicular to said first direction, said packing material maintaining said rigid single piece first size configuration until completely inserted into said nasal cavity wherein only upon contact with said fluid does expansion to said second size occur;
   barrel means having a bore for containing said packing material of said first size and having an inlet end and an outlet end, said packing material exiting said outlet end when being inserted into the nasal cavity and wherein said outlet end has a cross-sectional area substantially corresponding to said cross-sectional area of said packing material substantially throughout the length of said packing material;
   plunger means disposed in said barrel means and movable relative thereto, said plunger means being received in said inlet end of said barrel means and being movable to force said packing material from said outlet end for insertion into the nasal cavity, said plunger means including a shaft having an end surface, said packing material end surface being positioned forward of said plunger means shaft end surface in said barrel means, said plunger means shaft end surface contacting and terminating at said packing material end surface wherein said plunger means shaft end surface does not extend past and into said packing material when said packing material is being moved relative to said barrel means;
   attaching means connected adjacent to said end surface of said packing material for use in removing said packing material from the nasal cavity, said attaching means having substantial portions located exteriorly of said shaft of said plunger means when said plunger means is disposed in said barrel means; and
   wherein, when said packing material is being placed in the nasal cavity, said larger dimension in cross-section of said packing material is positioned in a substantially vertical direction for receipt by the nasal cavity.

2. The nasal pack syringe of claim 1 wherein:
   at least a first rib is longitudinally disposed along an interior surface of said barrel means to minimize friction of said packing material during movement thereof in said barrel means and said packing material has an outer surface for engaging said first rib wherein said outer surface is substantially smooth where said outer surface engages said first rib during movement of said packing material relative to said barrel means and said barrel means has substantially the same cross-sectional area throughout its length including at said inlet end of said barrel means.

3. The nasal pack syringe of claim 1 wherein:
   said plunger means includes a shaft and retention means, said retention means including two prongs having outer edges which extend laterally out from said plunger means shaft and wherein the lateral extent defined by said two prongs is greater than the width of said plunger means shaft in order to provide sufficient friction to retain said plunger means in said barrel means and yet allow said plunger means to slide within said barrel means and wherein said two prongs are made of a flexible material and with each of said prongs engaging portions of said barrel means during movement of said packing material relative to said barrel means.

4. A method for reducing bleeding and applying pressure in a nasal cavity using a nasal pack syringe, comprising:
   providing a barrel, said barrel having an inlet end and an outlet end;
   providing a plunger, said plunger including a shaft having an end surface;
   providing absorbent, packing material of a first size to fit and move within said barrel, said packing material including an end surface and being a single piece material and rigid, said packing material having a cross-section wherein said cross-section substantially throughout the length of said packing material has a larger dimension in a first direction than the largest dimension of said cross-section in a direction substantially perpendicular to said first direction, the cross-section area of said packing material substantially along its length substantially corresponding to the cross-sectional area of said outlet end of said barrel means;
   providing attaching means for said packing material wherein said attaching means is a separate material from and attached to said packing material;
   locating said packing material in said barrel;
   positioning a portion of said plunger in said barrel;
   contacting said end surface of said shaft of said plunger means and said end surface of said packing material wherein said plunger means shaft end surface terminates at said packing material end surface and in which said plunger means shaft end surface does not extend past and into said packing material;

positioning substantial portions of said attaching means exteriorly of said shaft of said plunger means;
positioning said packing material relative to the nasal cavity wherein said dimension of said cross-section of said packing material having the larger extent is positioned substantially vertical relative to the nasal cavity;
inserting said packing material in the nasal cavity by applying a force to said plunger;
maintaining said end surface of said plunger shaft in contact with said end surface of said packing material but exteriorly of said packing material during movement of said packing material relative to said barrel;
receiving said packing material in the nasal cavity;
removably fixing said attaching means to a facial feature in order to facilitate subsequent removal of said packing material from said nasal cavity by pulling on said attaching means.
absorbing fluid in the nasal cavity using said packing material thereby expanding said packing material to a second size and;
applying pressure to portions defining the nasal cavity using said expanded packing material.

* * * * *